United States Patent [19]

Washecheck

[11] Patent Number: 5,223,471
[45] Date of Patent: Jun. 29, 1993

[54] FLUORINE-CONTAINING MATERIALS

[75] Inventor: Don M. Washecheck, Naperville, Ill.

[73] Assignee: Amoco Corporation, Chicago, Ill.

[21] Appl. No.: 795,691

[22] Filed: Nov. 21, 1991

Related U.S. Application Data

[62] Division of Ser. No. 626,448, Dec. 12, 1990, Pat. No. 5,105,046.

[51] Int. Cl.$^5$ .................. B01J 27/12; B01J 27/125; B01J 27/138; C01F 11/22
[52] U.S. Cl. .................................. 502/226; 423/490
[58] Field of Search ................. 502/224, 231, 226; 423/490

[56] References Cited

U.S. PATENT DOCUMENTS

| 4,005,048 | 1/1977 | Dowden et al. | 502/226 X |
| 4,931,172 | 6/1990 | Kobos et al. | 204/418 |
| 4,948,680 | 8/1990 | Madou et al. | 429/13 |

OTHER PUBLICATIONS

Chemical Abstracts, vol. 110, pp. 468 and 731 (1989); vol. 111, p. 742 (1989); and vol. 114, p. 602 (1991).
Alfa Catalogue, 1986–1987, Morton Thiokol, Inc., Danvers, MA, 1986, pp. 51, 351, 508, 530, and 627.
Ivanov–Shits et al., "Specific Features of Ion Transport in Nonstoichiometric SrRF Phases", Solid State Ionics, 31 (1989), 253–268.
Ivanov–Shits et al., "Specific Features of Ion Transport in Nonstoichiometric Fluorite-Type BaRF Phases", Solid State Ionics, 31 (1989), 269–280.
CA 114(12):107465e (1991).
CA 108(20):177426t (1988).

Primary Examiner—W. J. Shine
Assistant Examiner—Douglas J. McGinty
Attorney, Agent, or Firm—Scott P. McDonald; Richard A. Kretchmer; Frank J. Sroka

[57] ABSTRACT

A contact material of a fluorine-containing compound of at least one of Sr, Ba, Sc, Y or La, as well as such contact material compositions themselves, is provided.

2 Claims, No Drawings

FLUORINE-CONTAINING MATERIALS

This is a division, of application Ser. No. 07/626,448, filed Dec. 12, 1990, now U.S. Pat. No. 5,105,046.

BACKGROUND OF THE INVENTION

This invention relates generally to the utilization of lower alkanes and the synthesis of hydrocarbons therefrom and, more specifically, to the oxidative conversion of low molecular weight alkanes, such as methane, to higher molecular weight hydrocarbons.

As the uncertain nature of ready supplies of and access to crude oil has become increasingly apparent, alternative sources of hydrocarbons and fuel have been sought out and explored. The conversion of low molecular weight alkanes (lower alkanes) to higher molecular weight hydrocarbons has received increasing consideration as such low molecular weight alkanes may be generally available from more readily secured and reliable sources. Natural gas, partially as a result of its comparative abundance, has received a large measure of the attention that has focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of coal, tar sands, oil shale and biomass, for example.

Today, much of the readily accessible natural gas generally has a high valued use as a fuel whether in residential, commercial or in industrial applications. Additional natural gas resources, however, are prevalent in many remote portions of the world, such as remote areas of Western Canada, Africa, Australia, U.S.S.R. and Asia. Commonly, natural gas from these remote resources is referred to as "remote natural gas" or, more briefly, "remote gas."

In many such remote regions, the widespread, direct use of the natural gas as a fuel is generally not currently profitable. Further, the relative inaccessibility of gas from such resources is a major obstacle to the more effective and extensive use of remote gas as the transportation of the gas to distant markets wherein the natural gas could find direct use as a fuel is typically economically unattractive.

Of course, while the primary current use of natural gas is as a fuel, natural gas may alternatively be used as a feedstock for chemical manufacture. In fact, natural gas is a primary chemical feedstock for the manufacture of numerous chemicals, such as methanol, ammonia, acetic acid, acetic anhydride, formic acid, and formaldehyde, for example. However, the markets for such chemicals are fairly limited in size. Consequently, methods for converting low molecular weight alkanes, such as those present in remote natural gas, to higher molecular weight hydrocarbons, preferably, to more easily transportable liquid fuels for which the world market is relatively large and/or elastic, are desired and a number of such methods have been proposed or reported.

Conversion of natural gas to liquid products is a promising solution to the problem of more effectively and efficiently utilizing low molecular weight hydrocarbons from remote areas and constitutes a special challenge to the petrochemical and energy industries. The dominant technology currently employed for the utilization of remote natural gas involves conversion of the natural gas to a liquid form via the formation of synthesis gas, i.e., a process intermediary composed of a mixture of hydrogen and carbon monoxide also commonly referred to as "syngas." In syngas processing, methane, the predominant component of natural gas, although typically difficult to activate, is reacted with oxygen or oxygen-containing compounds such as water or carbon dioxide to produce syngas which in turn is then converted to desired products.

Syngas processing, however, is relatively costly as the production of syngas and the subsequent conversion of the syngas are typically very capital intensive processing schemes. Further, while some of the products to which syngas can be converted, such as methanol, mixed alcohols, acetic acid, etc., contain oxygen and are thus logical products for production via syngas processing, hydrocarbon products such as gasoline and diesel fuel typically do not contain oxygen and consequently the production of such materials via syngas processing requires the additional processing step of oxygen removal. The addition and later removal of oxygen when such products are produced via syngas processing ultimately increases production costs.

When hydrocarbon products such as gasoline and diesel fuel are sought, the syngas mixture can be converted to syncrude, such as with Fischer-Tropsch technology, and then upgraded to the desired transportation fuels using typical refining methods. Alternatively, syngas can be converted to liquid oxygenates which can be blended with conventional transportation fuels to form materials such as gasohol, used as alternative fuels or converted to conventional transportation fuels by catalysts such as certain zeolites.

Because syngas processing typically requires high capital investment, with syngas typically being produced in energy intensive ways such as by steam reforming where fuel is burned to supply the heat of reforming, and represents an indirect means of higher hydrocarbon production (i.e., such processing involves the formation and subsequent reaction of the syngas intermediaries), other means for converting lower alkanes directly to higher hydrocarbons have been sought.

Oxidative coupling has been recognized as a promising approach to the problem of conversion of lower alkanes to higher molecular weight hydrocarbons. The mechanism of action of oxidative coupling processing, however, has not been clearly identified or defined and is not clearly understood. In such oxidative coupling processing, a low molecular weight alkane or a mixture containing low molecular weight alkanes, such as methane, is contacted with a solid material referred to by various terms including catalyst, promoter, oxidative synthesizing agent, activator or contact material. In such processing, the methane is contacted with such a "contact material" and, depending on the composition of the contact material, in the presence or absence of free oxygen gas, and is directly converted to ethane, ethylene, higher hydrocarbons and water. Carbon dioxide formation, which is highly favored thermodynamically, is an undesired product, however, as the formation of carbon dioxide results in both oxygen and carbon being consumed without production of the desired higher value $C_2+$ hydrocarbons.

In most cases of oxidative coupling processing, carbon monoxide and hydrogen are coproduced in addition to desired $C_2+$ hydrocarbons. If desired, such coproduced hydrogen can be used alone, in part or in its entirety, or supplemented with hydrogen from another source to effect conversion of carbon oxides to produce methane. Such produced methane can, in turn, be recycled. Alternatively, the hydrogen can be used to effect conversion of carbon monoxide to carbon-containing oxygenates such as methanol or mixed alcohols (e.g., a mixture of one or more alcohols such as methanol, ethanol, propanols and butanols) or higher hydrocarbons such as a mixture of paraffins and olefins typically produced in the process commonly known as Fischer-Tropsch synthesis. Alternatively or in addition, such coproduced carbon monoxide and hydrogen can, if desired, be combined with olefins, such as those produced during the oxidative coupling processing, to produce various oxygenates, such as acetone or propanol, for example. As described above, however, the production of materials such as oxygenates from carbon monoxide and hydrogen (i.e., synthesis gas) is not a direct approach for the utilization of natural gas, as such processing still involves the use of the syngas intermediaries.

Many patents describe processes for converting methane to heavier hydrocarbons in the presence of reducible metal oxide catalysts. During such processing, the reducible metal oxide "catalyst" typically is reduced and thus most of these patents require or imply the need for a separate stage to reoxidize the catalyst.

For example, U.S. Pat. No. 4,444,984 discloses a method for synthesizing hydrocarbons wherein methane is contacted with a reducible oxide of tin at an elevated temperature. Such contact results in the tin oxide being reduced. The reduced composition is then oxidized with molecular oxygen to regenerate a reducible oxide of tin.

U.S. Pat. No. 4,495,374 discloses the use of a reducible metal oxide promoted by an alkaline earth metal in such a method of methane conversion. During such processing, the reducible metal oxide of the promoted oxidative synthesizing agent is reduced. The reduced oxidative synthesizing agent can then be removed to a separate zone wherein it is contacted with an oxygen-containing gas to regenerate the promoted oxidative synthesizing agent.

Examples of other such patents include: U.S. Pat. No. 4,523,049, which shows a reducible oxide catalyst promoted by an alkali or alkaline earth metal, and requires the presence of oxygen during the oxidative coupling reaction; U.S. Pat. No. 4,656,155, which specifies yttrium in a mixture requiring zirconium and alkali metal; U.S. Pat. No. 4,450,310, which is directed to coupling promoted by alkaline earth metal oxides in the total absence of molecular oxygen; and U.S. Pat. No. 4,482,644, which teaches a barium-containing oxygen-deficient catalyst with a perovskite structure.

Additional patents and publications describe oxidative coupling of methane using alkaline earth metal-containing halide catalysts. These include:

"Oxidative Coupling of Methane with Alkaline Earth Halide Catalysts Supported on Alkaline Earth Oxides," by K. Fujimoto, S. Hashimoto, K. Asami and H. Tominaga, *Chemistry Letters*, pp. 2157–2160, (1987); "Selective Oxidative Coupling of Methane Over Supported Alkaline Earth Halide Catalyst, " by K. Fujimoto, S. Hashimoto, K. Asami, K. Omata and H. Tominago, presented at the Sep. 1-2, 1988 Bicentennary Catalysis Conference at Sydney, Australia; and "Selective Oxidative Coupling of Methane Over Supported Alkaline Earth Metal Halide Catalyst," Applied Catalysis, 50 (1989), 222–236, K. Fujimoto, S. Hashimoto, K. Asami, K. Omata and H. Tominaga, which discuss coupling of methane with alkaline earth halide catalysts supported on alkaline earth oxides. Most of the work presented in these papers focus on the halide chloride. The only fluoride-containing materials examined were: NaF/MgO, $MgF_2$/MgO and $CaF_2$/CaO, with catalyst performance for the tested materials measured at 15 minutes after the start of the reaction. The fluoride catalysts were prepared by fluoriding the surface of calcium and magnesium oxides by treating them with hydrofluoric acid. Enough acid was added in this fashion to produce a 5 wt. %, as metal halide, loading of each compound. In fact, the 1987 paper states that the promoting effect of halide doping was Cl > Br > F. Both the 1987 and 1989 papers state: "It is clear that $MgF_2$ is a negative catalyst for MgO." They also report that it is not likely that methane is activated by a metal halide that is supported or supplied from the vapor phase.

In these papers, $MgCl_2$/CaO was identified as the most effective, of the materials studied, for the oxidative coupling of methane. The papers identify the loss of $Cl^-$ from the material and that deactivation of $C_2$ formation can be attributed to the loss of halide ion. The researchers added chloride to the feed on recognizing that chloride was being lost from the catalysts while on stream.

Halogen loss from a catalyst or contact material, such as in the form of a halide, particularly in the presence of water as commonly results from oxidative coupling, can result in a very corrosive effluent stream. To permit the safe handling of such corrosive streams, corrosion resistant materials of construction are required. Substituting corrosion resistant materials of construction for typical construction materials almost invariably increases the capital expenditures required for a facility.

An additional concern relative to the use of a catalyst or contact material which experiences the loss of halogen, is possible formation of even trace amounts of undesirable halogenated compounds such as halogenated aromatics, such as chlorinated phenols and chlorinated biphenyls, (PCB's), for example. These halogenated compounds are generally undesired as they raise various health concerns.

Accordingly, contact materials should be halogen-free or not lose significant amounts of halogen when the contact material is subjected to oxidative coupling reaction conditions.

As a class of materials, halides tend to have significantly lower melting points, as compared to their oxide counterpart, with fluorides generally tending to have the highest melting points of the halides. For example, barium chloride ($BaCl_2$) and barium fluoride ($BaF_2$) have melting points of 963° C. and 1355° C., respectively, while barium oxide (BaO) has a melting point of 1918° C. Typically, processes for the oxidative coupling of lower alkanes operate at relatively high temperatures (e.g., 750° C. to 900° C.) and yet the contact material must remain hard to maintain the crystal integrity of the material in the reactor. The presence of a low melting point contact material or contact material component can result in the loss of performance by the contact material due to the contact material losing surface area or desired or needed components through volatilization. For fluidizable contact materials, the presence of a molten or "soft" component or material can result in the small fluidizable particles adhering to one another upon passing to cooler regions of the reactor or the process. Masses of such multiple particle, adhered materials are generally not suited for use in fluid bed operations as such masses will tend to sink to the bottom of the reactor vessel.

Thus, there is a need that the contact material exhibit and maintain physical integrity when subjected to oxidative coupling reaction conditions.

SUMMARY OF THE INVENTION

The general object of this invention is to provide an improved oxidative conversion process and oxidative coupling contact material.

It is an object of the present invention to overcome one or more of the problems described above.

The general object of this invention can be attained by a method for converting lower alkanes to a product composition including a higher molecular weight hydrocarbon which method includes contacting a feed composition including lower alkanes with an oxidative coupling contact material including a fluorine-containing compound of at least one of the elements, Sr, Ba, Sc, Y or La. Such contacting is done in the presence of oxygen and at oxidative coupling reaction conditions.

In addition to the method of conversion of lower alkanes to higher molecular weight hydrocarbons, the invention comprehends novel oxidative coupling contact material compositions which include at least one fluorine-containing compound of an element selected from the group consisting of Sr, Ba, Sc, Y and La.

The invention further comprehends methods for converting $C_1$–$C_3$ alkanes to a product composition including a higher molecular weight hydrocarbon wherein a feed composition including $C_1$–$C_3$ alkanes is contacted with an oxidative coupling contact material including fluorine-containing compounds of Sr and Ba, respectively. Such contacting is done in the presence of oxygen and at oxidative coupling reaction conditions. The invention also comprehends these oxidative coupling contact material compositions of fluorine-containing compounds of Sr and Ba, respectively.

As used herein, the term "reducible" is used to identify those oxides of metals which are reduced by contact with $C_1$–$C_3$ alkanes at temperatures within the range of about 500° C. to about 1,000° C.

The term "catalytically effective" refers to the ability of the material in question to increase chemical reactivity for the formation of hydrocarbons in preference to carbon oxide (CO and $CO_2$) formation.

The terms "oxide" and "oxides" includes the various oxygen-containing compositions including sulfates, phosphates, carbonates, titinates and zirconates, for example.

The term "lower alkane" as used herein refers to $C_1$–$C_3$ alkanes.

The term "oxidative coupling contact material" or "contact material," for short, as used herein refer to a material which when contacted with a lower alkane and oxygen at oxidative coupling contact conditions results in the formation of hydrocarbons having a higher molecular weight than the original feed alkane.

The term "cofeed" operation as used herein refers to that mode of conversion operation wherein the oxidative coupling contact material is simultaneously contacted by the lower alkane(s) and oxygen (such as in the form of an oxygen-containing gas). In such operation, the lower alkane(s) and the oxygen can be mixed together before or during their contact with the contact material.

The term "redox" operation as used herein refers to that mode of conversion operation wherein the oxidative coupling contact material is sequentially contacted by the lower alkane(s), followed by contact with oxygen (such as in the form of an oxygen-containing gas). In such operation, the lower alkane(s) and oxygen are generally not mixed together to any substantial extent either before or during contact with the contact material. In some process designs, however, some such "carryover" or inadvertent mixing of the lower alkanes and oxygen may occur.

The term "gasoline-type hydrocarbon products" as used herein refers to those hydrocarbons having a boiling point in the general range of $C_4$ hydrocarbons to about 450° F., inclusive.

The term "counter cation" as used herein refers to a positively charged ion which serves to balance the charge on a corresponding anion.

The term "fluoride" as used herein refers to a material wherein a majority of the counter anions are $F^-$ and includes materials such as oxyfluorides.

The term "stability" as used herein in reference to fluorine-containing contact material refers to the ability of the material to be subjected to oxidative coupling reaction conditions for the conversion of lower alkanes to higher molecular weight hydrocarbons without undergoing significant or substantial loss of fluorine over a reasonable time period of operation, e.g., the material loses no more than about 20% of its fluorine content over an operational time period of 50 hours.

The term "substantially free" as used herein to describe the contact material generally indicates that the contact material excludes amounts of the specified material(s) which materially affect the effectiveness of the contact material in the oxidative conversion processing.

Other objects and advantages of the invention will be apparent to those skilled in the art from the following detailed description taken in conjunction with the appended claims.

DETAILED DESCRIPTION OF THE INVENTION

According to the invention, an oxidative coupling contact material and a method for converting lower alkanes to higher molecular weight hydrocarbons are provided. The invention contemplates an oxidative coupling contact material composition which includes at least one fluorine-containing compound of an element such as Sr, Ba, Sc, Y and La and a method of alkane conversion generally applicable to alkanes containing from one to three carbon atoms. It is to be understood, however, that while the method may be utilized with higher alkane feedstocks, such use may, as a result of competing reaction kinetics, result in a reduction in the amount of higher molecular weight hydrocarbons formed thereby.

In one preferred embodiment of the invention, methane, illustrative of a lower molecular weight alkane feedstock useful in the practice of the invention, is mixed with air, as a source of oxygen, and the resulting mixture is contacted with a suitable oxidative coupling contact material, as described below, for the oxidative coupling of the aforesaid alkane. Thus, the invention will be described herein with reference to conversion wherein the lower alkanes converted to higher molecular weight hydrocarbons are methane. It is to be understood, however, that feedstocks typically useful in the practice of the invention will include lower alkanes such as methane, ethane or propane (i.e., $C_1$–$C_3$ alkanes) either alone, separately or in mixtures with each other, with or without the presence of other materials, such as inert gases, e.g., $N_2$ or minor amounts of other hydrocarbon materials, for example. Natural gas is an example of a feedstock which while containing predominantly methane can and typically does contain at least minor amounts of the other above-identified lower alkanes as well as other materials such as nitrogen gas and carbon dioxide, for example.

It is also to be understood that sources or forms of oxygen-containing gas other than air may be used or preferred in the practice of the invention. Thus, the oxygen-containing gas for use in the method of this invention can vary in molecular oxygen content from oxygen-depleted air, to air, to oxygen gas itself, for example. Air or enriched air may be a preferred source of molecular oxygen. The oxygen-containing gas should preferably provide a gas-vapor effluent mixture from the oxidative coupling reactor which preferably avoids the flammability limits for such mixtures. It is to be understood, however, that the amount of oxygen gas in a flammable mixture is generally dependent on a number of factors and conditions such as temperature, pressure, presence of inert gases, and oxygen concentration, for example. Thus, in practice using standard operating conditions of a temperature of about 800° C. and pressure of about 1 atmosphere, a conversion reactor effluent mixture containing (measured on a solid-free basis) no more than about 2 to about 8 volume percent of oxygen may be preferred. It is to be understood, however, that some types of conversion reactors, such as fluid bed conversion reactors, for example, may be capable of safe operation in the flammable range, at least under some modes or other conditions of operation.

Such oxidative coupling processing of methane, when air is used as a source of oxygen, typically results in a gaseous mixture comprising ethane and ethylene, illustrative of saturated and unsaturated aliphatic hydrocarbon products having higher molecular weights than the feedstock alkanes from which they were formed, and possibly some traces of aromatics or higher hydrocarbons which may form in the reactor, such as at high operating temperatures, for example, at temperatures greater than 750° C., as well as carbon monoxide, carbon dioxide, nitrogen, water, any remaining unreacted feedstock alkane and oxygen. It being understood that conventional catalytic processing schemes, such as refining hydrotreatment, are typically conducted at operating temperatures of only about 700° C. to 800° F.

Such a reaction product mixture may illustratively be used as chemical feedstock or be further reacted, such as occurs during conversion, to form gasoline type hydrocarbon products. For example, the effluent with desired or required pretreatment, e.g., $H_2O$ removal, and/or downstream treatment, e.g., $N_2$ removal, may be passed over a suitable aromatization/oligomerization catalyst (such as a crystalline borosilicate or aluminosilicate molecular sieve materials or supported phosphoric acid) to produce desired gasoline type hydrocarbon products. Other specific uses of the reactor effluent will be apparent to those skilled in the art.

In the above-described embodiment, methane and oxygen (as a part of air) are simultaneously contacted with the oxidative coupling contact material. Such operation is commonly referred to as "cofeed" operation and in such operation, oxygen, which may be needed for the coupling reaction to occur, rather than exclusively being carried into the reactor via the lattice of the contact material, as may be typical of "redox" operation, as described above, is also fed to the reactor. Further, cofeed operation may minimize or eliminate the need for subsequent reoxidation of the contact material such as may be required to resupply lattice oxygen to contact materials such as those which typically contain reducible metal oxides as typically is required when such contact materials are utilized in a redox mode operating scheme.

Generally, a suitable feedstock for the method of this invention comprises at least one of methane, ethane and propane and preferably comprises mostly methane, e.g., at least about 75 percent methane, and more preferably may be methane as methane is typically the predominant reserve component which is desired to be converted to a higher molecular weight hydrocarbon. Thus, a suitable feedstock for the method of this invention comprises natural gas, gases formed during mining operations and petroleum processes or in the above- or below-ground gasification or liquefaction of coal, tar sands, oil shale and biomass, for example.

The contacting of the feedstock with the oxygen-containing gas in the presence of the contact material generally is performed at oxidative coupling reaction conditions including temperature and pressure. Preferably, such contacting is performed at a temperature in the range of from about 600° C. to about 1000° C. and, more preferably, in the range of from about 700° C. to about 900° C. These temperature ranges have been found to be preferred as operation at temperatures below about 600° C. may generally result in the contact material having relatively unfavorable selectivities while operation at higher temperatures, e.g., temperatures greater than about 900° C., may result in generally undesirable thermal reactions seriously competing with coupling reactions. The products resulting from such thermal reactions will typically be largely comprised of $H_2$, $CO_x$ (where $x=1$ or 2) and may also include coke, acetylene and aromatics such as benzene, for example. Such thermal reactions will typically overwhelm the generally desirable coupling reactions when temperatures exceed about 1000° C. It is to be understood, however, that at higher reaction temperatures at least trace quantities of aromatic compounds may also form.

The contacting of the feedstock and oxygen with the contact material is preferably performed under a total absolute pressure in the range of from about 1 atmosphere to about 10 atmospheres, and more preferably in the range of from about 1 atmosphere to about 5 atmospheres, as operation at pressures exceeding this range typically results in reduced $C_2+$ product selectivities while subatmospheric operation is believed to be economically unattractive as capital expenditures escalate rapidly for a system to be capable of handling the actual volumes of gas required for such a commercial operation.

The ratio of the partial pressure of the combined feedstock alkanes containing from 1 to 3 carbon atoms to the oxygen partial pressure at the entrance of the reactor in the contacting step is preferably in the range of from about 2:1 to about 40:1 and, more preferably, in the range of from about 2:1 to about 10:1, as operation at lower $C_1$-$C_3$ alkane to oxygen partial pressure ratios generally results in excessive carbon oxide formation, while operation at higher ratios may result in insufficient amounts of oxygen being present to obtain desired levels of conversion and consequently results in the remainder of greater amounts of unreacted hydrocarbon reactant. The combined partial pressures of the alkanes in the feedstock containing from 1 to 3 carbon atoms at the entrance to the first reactor (the contacting reactor) is preferably no more than about 10 atmospheres, and, more preferably, no more than about 4 atmospheres. The oxygen partial pressure at the entrance to the first reactor is preferably no more than about 4 atmospheres and, more preferably, no more than about 2 atmospheres. The oxygen partial pressure in the gaseous effluent from the reactor in the contacting step is preferably substantially 0.

Also, the contacting step is preferably performed at a space velocity of from about 100 to about 20,000 volumes of total feed gas at ambient conditions per volume of catalytic composition per hour and more preferably at a space velocity of about 800 to about 8000 volumes of total feed gas per volume of catalytic composition per hour, as thermal reactions will generally predominate with operation at lower space velocities while oxygen conversion will generally be unsuitably incomplete with operation at higher space velocities.

A preferred contact material useful in the practice of the invention preferably contains at least one fluorine-containing compound of Sr, Ba, Sc, Y and La. Preferred fluorine-containing oxidative coupling contact material compositions comprise a fluorine-containing compound of Sr and Ba, respectively. Such fluorine-containing compounds preferably are fluorides of Sr and Ba, and preferably exhibit ratios of fluoride to either strontium or barium, respectively, of about 2 to 1, as these materials have exhibited comparatively greater stability at oxidative coupling reaction conditions, as compared to other fluorine-containing compounds and, more specifically, as compared to other fluorides.

Fluorine has the greatest electronegativity (electron affinity) of any element. Additionally, the fluorine anion is relatively small compared to the chloride anion and is comparable to the oxide dianion (ionic radii: $F^- = 1.33$ Angstroms, $O^{2-} = 1.32$ Angstroms and $Cl^- = 1.81$ Angstroms). These properties of fluorine tend to result in such fluorine-containing oxidative coupling contact material compositions having higher sintering stability (reflected by the compositions having higher melting points) and greater resistance to hydrolysis, as compared to corresponding chloride-containing materials. For example, $SrCl_2$ melts at 875° C. and has a solubility of about 54 grams/100 cc of water. $SrF_2$ on the other hand, melts at 1473° C. and has a solubility of only about 0.01 grams/100 cc of water.

It is speculated that the high electronegativity of fluorine alters the properties of the counter cation by greater polarization of the cation, and may also affect the bonding energy of any adsorbed species. These changes can alter the selectivity of the contact material.

An oxidative coupling contact material of the invention can include a fluorine-containing compound of at least one Group IIIB metal of the Periodic Table selected from the group consisting of Sc, Y and La. In an alternative embodiment, the Group IIIB metal of the Periodic Table of such composition is either Y or La.

In one embodiment of the invention the fluorine-containing oxidative coupling contact material, in addition to at least one of Sc, Y, or La or, in the alternative embodiment, either Y or La, will additionally include Mg.

In another embodiment of the invention, the fluorine-containing oxidative coupling contact material compounds of at least one Group IIIB metal of the Periodic Table selected from the group of Sc, Y and La will also contain Ca.

In one embodiment of the contact material including a fluorine-containing compound of at least one of Sc, Y or La, the contact material will also include either Sr or Ba. In a preferred embodiment of such a composition, the Group IIIA metal of the Periodic Table of such composition will be either Y or La. Such preferred oxidative coupling contact materials include those exhibiting ratios of fluoride to strontium or barium, respectively, to yttrium or lanthanum, respectively, of about 7 to about 2 to about 1, respectively, for example, such as $YSr_2F_7$, La $Sr_2F_7$, Y $Ba_2F_7$, and La $Ba_2F_7$.

In addition, the fluorine-containing oxidative coupling contact material compositions of the invention, particularly fluoride oxidative coupling contact material compositions, will preferably be substantially free of a catalytically effective reducible metal oxide, as reduction of a contact material can lead to a loss in the selectivity of the contact material to desired higher molecular weight hydrocarbons.

The following examples illustrate the practice of the invention. It is to be understood that all changes that come within the spirit of the invention are desired to be protected and thus the invention is not to be construed as limited by these examples.

EXAMPLES

EXAMPLE 1

Preparation of a contact material of $BaF_2$ on a $Al_2O_3$ support

An oxidative coupling contact material was prepared by physically mixing two grams of barium fluoride powder, 99.9+% purity from Aldrich Chemical Co., Inc., with 8 grams of alpha alumina (30-50 mesh).

EXAMPLE 2

The contact material of Example 1 was loaded in a quartz reactor tube to form a bed with a quartz lined thermocouple in the bed of the contact material to facilitate temperature control. A mixture of 20% $O_2$ and 80% $N_2$ was blended with methane to provide a nominal 5:1 $CH_4$:$O_2$ feed blend. The feed was fed at a rate of 9000 scc/gm cat.-hour to the reactor tube, which was operated at 825° C. (1517° F.) for a period of time of 70 hours.

Results

A selectivity to $C_2+$ hydrocarbons of 73% to 74% was obtained. $C_2+$ hydrocarbon selectivity increased slightly during approximately the first 15 hours of operation and then stabilized at about 74%. During the first 15 hours of operation, oxygen conversion decreased from 85% to 75%. Over the next 60 hours of operation, oxygen conversion decreased to 53% to 57%. As the run proceeded the rate of loss of catalyst activity decreased. In addition, selectivity was essentially constant after about 30 hours of operation, signifying that the contact material was at or near a steady state condition, i.e., if the material was going to lose a significant amount of fluorine it was expected it would have lost it during this period of operation, at least to the extent that such loss would be reflected in performance data for the contact material.

EXAMPLE 3

Samples of the contact material of Example 1 and the used contact material resulting from Example 2 (after 70 hours of use as described in Example 2) were analyzed by X-ray Photoelectron Spectroscopy, and the ratio of fluorine to barium was determined for these samples. The XPS data showed less than 1% change in the fluorine to barium ratio between the fresh and the used contact materials samples, indicating no significant loss in fluorine during use in the processing to produce higher molecular weight hydrocarbons.

|  | F/Ba atomic ratios |
| --- | --- |
| Fresh sample from Example 1 | 1.26 |
| Used sample from Example 2 | 1.25 |

(NOTE: Of course, the nominal F/Ba atomic ratio for $BaF_2$ is "2.0." The lower observed ratios are believed to have been due to the calibration of the XPS. The significance of the results, i.e., the lack of significant change of the F/Ba ratio between the fresh and used samples, is unaffected by the calibration of the XPS.)

Thus, the activity loss was believed due to changes in surface area and/or porosity. Deactivation by carbon, carbon oxide, or coke deposition is another possible explanation since the C/Ba atomic ratio was greater for the used contact material than for the fresh contact material.

EXAMPLE 4

Ultra pure strontium fluoride powder, from Aldrich Chemical Co., Inc., was used as a contact material. Conditions were the same as in Example 2 but now with the reactor tube loaded with only 0.5 gram of the fluoride. The feed was fed at a rate of 42,000 scc/gm cat.-hour and operation was done at a temperature of 825° C.

Results

Selectivity to $C_2+$ hydrocarbons increased from about 70% to about 75% over the first 10 to 15 hours of the run. Selectivity to $C_2+$ hydrocarbons then remained stable to the end of the run at 50 hours. Activity, as measured by oxygen conversion, decreased from 42% to 27% over the same initial 10 to 15 hour period. Oxygen conversion decreased more slowly over the balance of the 50 hour run period to about 20% at the end of the run, signifying that the contact material was at or near a steady state condition.

EXAMPLE 5

To test the hypothesis that $SrF_2$ and $BaF_2$ were deactivating by sintering (loss of surface area), a sample of $SrF_2$ powder was heated in nitrogen at 1600° F. for 4 days. This treating procedure would be expected to sinter the catalyst but not cause any conversion of the fluoride to oxides. A sample of the calcined $SrF_2$ was run at oxidative coupling conditions of 850° C. and a relative feed rate of 20,000 scc/gm cat.-hour. Oxygen conversion remained essentially constant at 30% over the 17 hour run; a period of time over which the unsintered contact material normally would be expected to lose activity most rapidly. The activity was less than the nonsintered contact material as expected if the surface area decreased. This experiment supports the belief that sintering was the primary initial deactivation mechanism and that fluoride loss was not involved in the deactivation.

EXAMPLE 6

XPS analysis of the used contact material resulting from the use of $SrF_2$ in Example 5, in which $SrF_2$ was calcined at 1600° F. under $N_2$ atmosphere, showed no loss of fluoride relative to a fresh uncalcined sample of $SrF_2$ based on the fluoride to strontium atomic ratio of the respective samples.

|  | F/Sr atomic ratios |
| --- | --- |
| $SrF_2$ (fresh) | 1.37 |
| Used sample from Example 5 | 1.27 |

(NOTE: Of course, the nominal F/Sr ratio for $SrF_2$ is "2.0." Consistent with Example 3, the lower observed ratios are believed to have been due to the calibration of the XPS. The significance of the results, i.e., the lack of significant change of the F/Sr ratio between the fresh and used samples, however, is unaffected by the calibration of the XPS.)

EXAMPLE 7

Preparation of contact material with Y:Sr:F in a mole ratio of about 1:2:7

Appropriate amounts of nitrates of strontium and yttrium were dissolved in water to give a 2:1 molar ratio of Sr to Y. A stoichiometric amount of ammonium fluoride was dissolved in water and added to the nitrate solution to form a white precipitate. Water was added to thin the gel and this was stirred overnight. The precipitate was filtered, dried at 120° C. overnight, and calcined at 1600° F. for 8 hours to give a very hard white material.

EXAMPLE 8

The contact material of Example 7 was crushed and sieved to 30-50 mesh and tested under conditions outlined in Example 2. For this contact material, the selectivity to $C_2+$ hydrocarbons increased with time as did oxygen conversion. No plateau was observed after 20 hours. With operation at 825° C. and a feed rate of 10,500 scc/gm cat.-hour at the end of 20 hours, selectivity to $C_2+$ hydrocarbons was 62% and oxygen conversion was 15%.

EXAMPLE 9

Yttrium fluoride powder, 99.9+% purity from Aldrich Chemical Co., Inc., was loaded in the reactor tube as an oxidative coupling contact material, as was done with the contact materials of Examples 1 and 2, for example.

A mixture of 40% $CH_4$, 4% $O_2$ and the balance $N_2$ was fed at a rate of 6000 scc/gm.cat.-hour to the loaded reactor tube. The reactor was operated at near atmospheric pressure and temperature ranging from 825° to 875° C.

Results

At 875° C., oxygen conversion was 72% and $C_2+$ hydrocarbon selectivity was 71%. Both oxygen conversion and selectivity to $C_2+$ hydrocarbons generally increased with increasing temperature.

EXAMPLE 10

Lanthanum fluoride powder, from Aldrich Chemical Col, Inc., was loaded in the reactor tube as a contact material, as was done with the contact material of Example 9.

Operating conditions were the same as those specified in Example 9.

Results

An oxygen conversion of about 100% was realized with operation at temperatures above 825° C. Selectivity to $C_2+$ hydrocarbons decreased slightly with increasing temperature. With operation at 825° C. the $C_2+$ hydrocarbon selectivity was 65%, while with operation at 875% the $C_2+$ hydrocarbon selectivity was 61%.

The foregoing detailed description is given for clearness of understanding only, and no unnecessary limitations are to be understood therefrom, as modifications within the scope of the invention will be obvious to those skilled in the art.

What is claimed is:

1. An oxidative contact material composition comprising a fluorine-containing compound of the Group IIIB metal Y and additionally comprising Mg, with said composition being substantially free of catalytically effective reducible metal oxides.

2. The composition which comprises $LaBa_2F_7$.